United States Patent [19]

Averette

[11] Patent Number: 5,012,845
[45] Date of Patent: May 7, 1991

[54] FLUID INJECTOR

[75] Inventor: Julius P. Averette, Baker, La.

[73] Assignee: Dynatech Precision Sampling Corporation, Baton Rouge, La.

[21] Appl. No.: 233,354

[22] Filed: Aug. 18, 1988

[51] Int. Cl.$^5$ ............................................. G01N 1/14
[52] U.S. Cl. ................................. 141/329; 141/130; 422/63; 422/103; 73/864.084; 73/864.087
[58] Field of Search ........... 73/863.81, 864.81–864.87, 73/864.21, 864.22, 864.24, 864.16, 864.17, 864.18, 864.11, 864.13, 863.84, 863.83; 141/27, 25, 65, 130, 66, 329, 330; 422/63, 103; 222/400.7, 400.8; 604/140, 147, 155, 411, 414

[56] References Cited

U.S. PATENT DOCUMENTS

| | | | |
|---|---|---|---|
| 2,541,272 | 2/1951 | Murphy | 141/329 |
| 2,786,468 | 3/1957 | Singer et al. | 604/155 |
| 3,699,348 | 10/1972 | Hocherl | 73/864.16 X |
| 4,094,195 | 6/1978 | Friswell et al. | 73/864.22 X |
| 4,094,197 | 6/1978 | Harris, Sr. et al. | 73/863.81 |
| 4,121,465 | 10/1978 | Harris, Sr. et al. | 73/863.81 |
| 4,199,543 | 4/1980 | Phillips | 73/864.22 X |
| 4,336,000 | 6/1982 | Jorgensen et al. | 73/864.16 X |
| 4,342,341 | 8/1982 | Lee | 141/330 |
| 4,475,666 | 10/1984 | Bilbrey et al. | 73/864.16 |
| 4,532,969 | 8/1985 | Kwaan | 141/27 |
| 4,555,957 | 12/1985 | Frankel et al. | 73/864.16 |
| 4,602,517 | 7/1986 | Schutz | 73/864.16 |
| 4,624,148 | 11/1986 | Averette | 73/864.21 |
| 4,713,974 | 12/1987 | Stone | 73/864.86 |
| 4,815,632 | 3/1989 | Ball et al. | 73/864.16 X |

Primary Examiner—Henry J. Recla
Assistant Examiner—Casey Jacyna
Attorney, Agent, or Firm—Llewellyn A. Proctor

[57] ABSTRACT

An automatic fluid injector, useful for the injection of preselected small, accurately measured quantities of fluid specimens into, e.g., an analytical instrument, particularly a purge and trap analyzer. The injector includes generally a syringe, or syringe assembly, inclusive of a barrel into which a fluid specimen can be loaded, a plunger for the displacement of the fluid specimen from said barrel via the dispensing end thereof into the analyzer, and a probe integral therewith for the pick up of the fluid specimen for filling the barrel of the syringe. The combination further includes a magazine for transporting one or more fluid specimen-containing septum sealed vials for pick up of a fluid specimen therefrom by the probe portion of the syringe assembly for delivery to the barrel of the syringe. It thus relates to improvements in a fluid injection apparatus, especially to the combination of a syringe and injector feed assembly, and further combination including a tubular valve assembly which provide a mechanism for delivery of a fluid specimen to an analytical instrument, and purge mechanism.

9 Claims, 14 Drawing Sheets

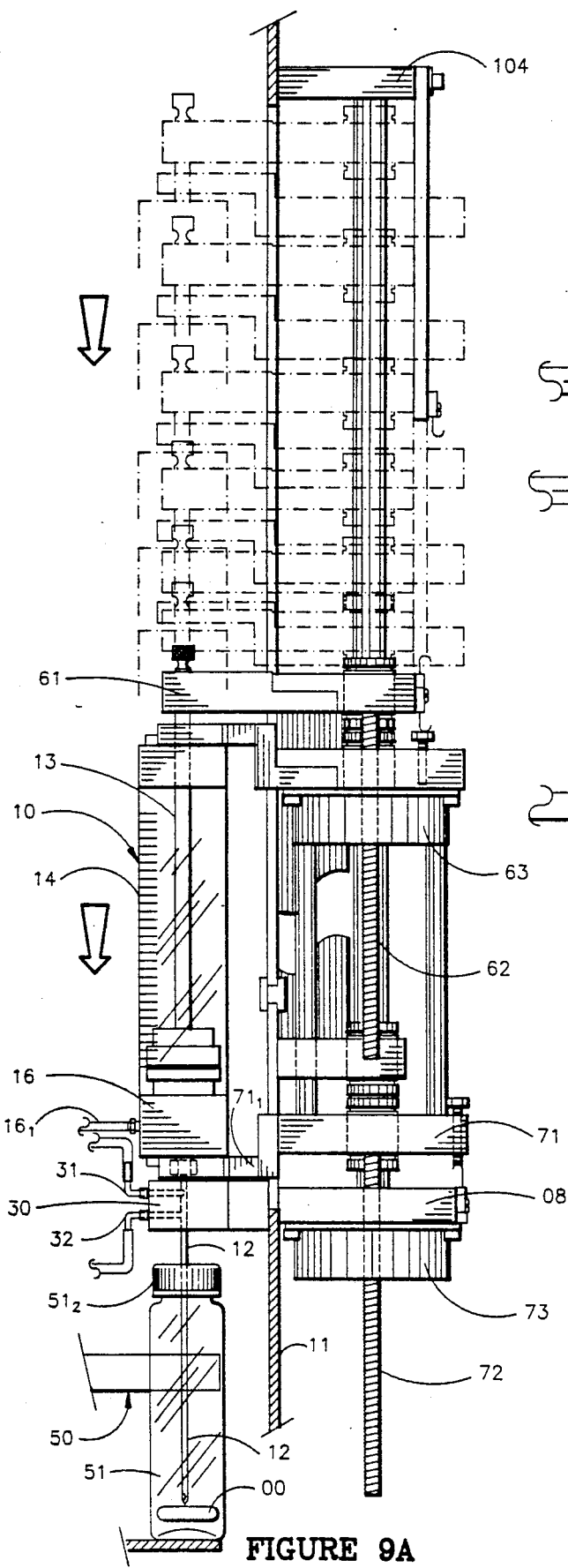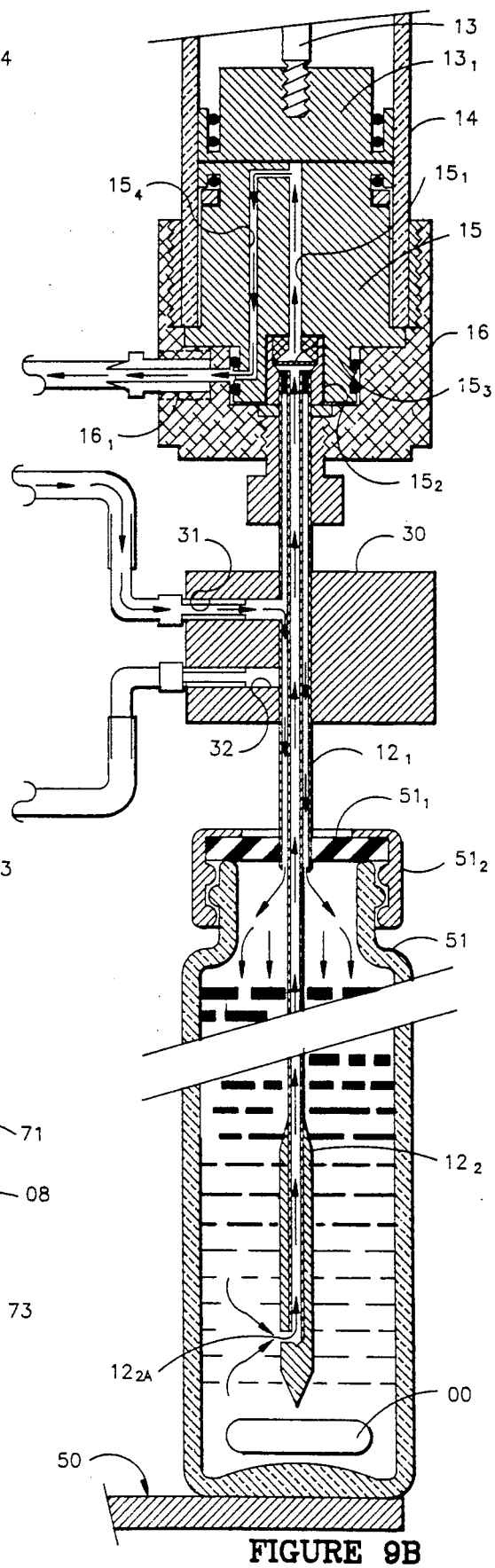
FIGURE 9A
FIGURE 9B

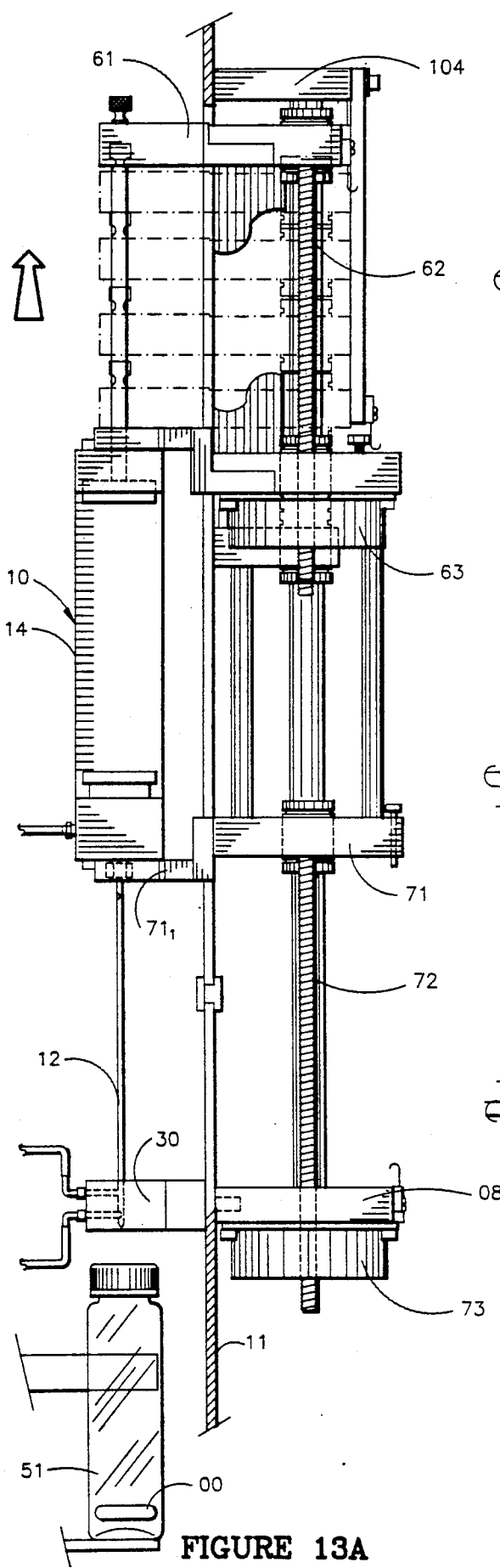
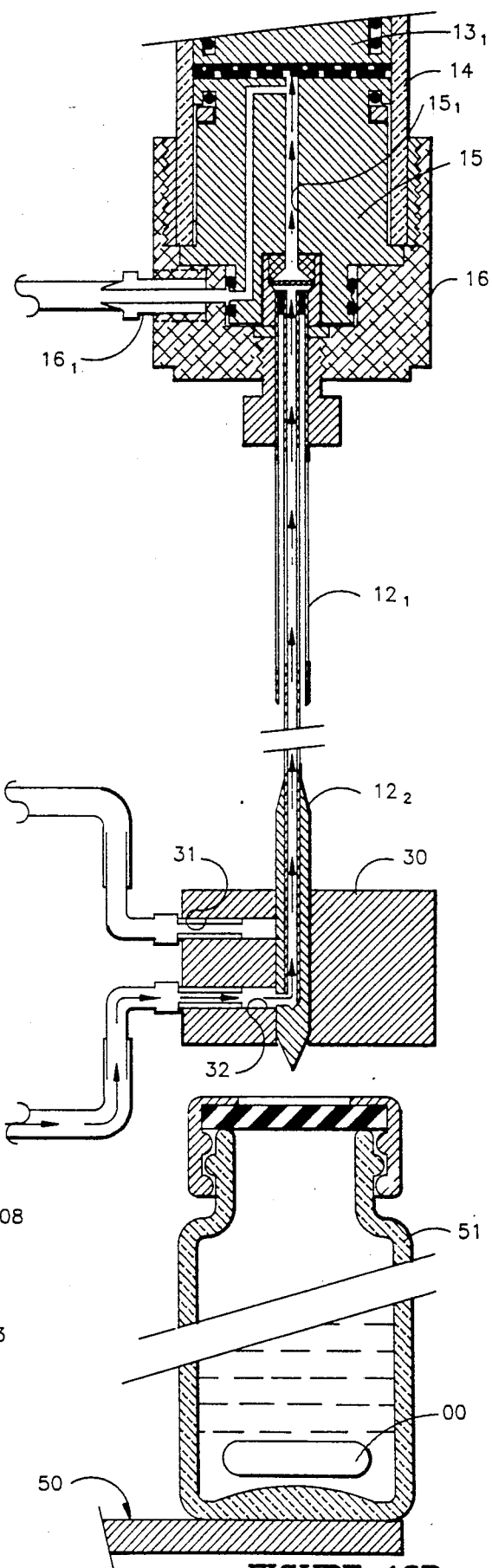
FIGURE 13A
FIGURE 13B

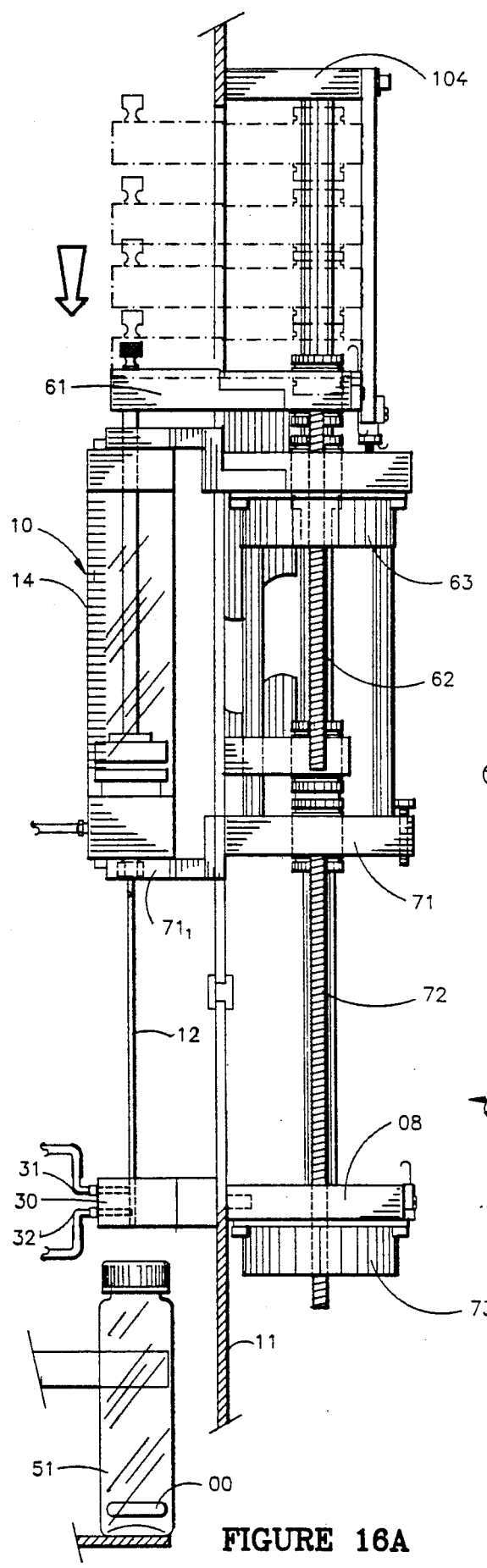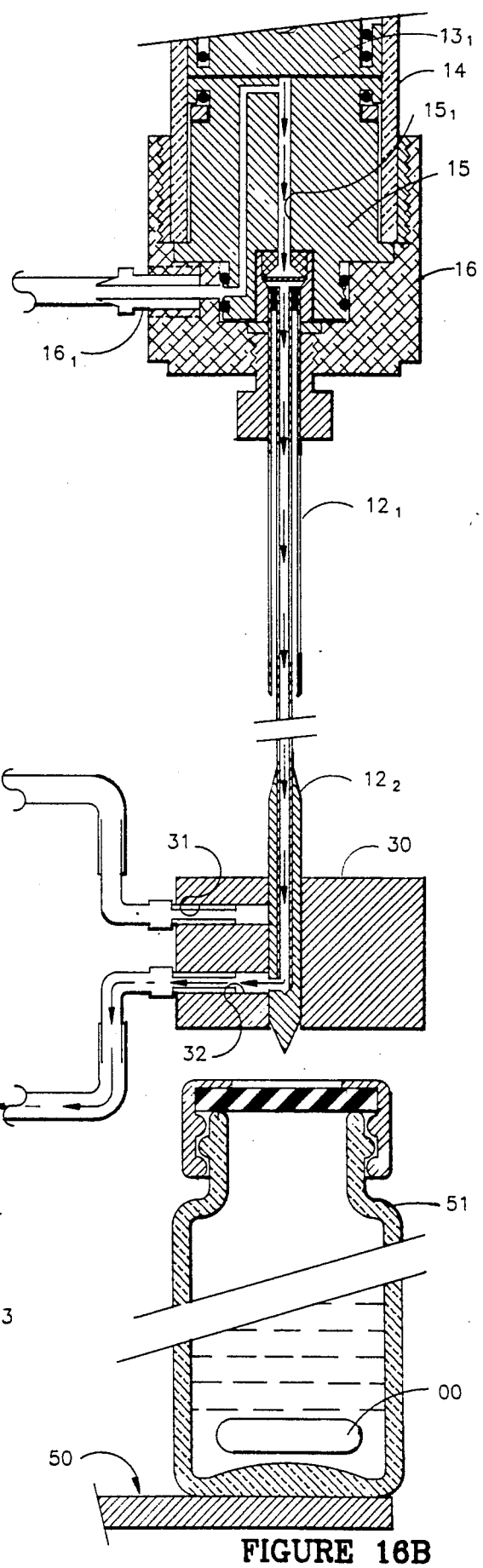
FIGURE 16A
FIGURE 16B

FLUID INJECTOR

FIELD OF THE INVENTION

This invention relates generally to automatic fluid injectors, or apparatus for the injection of accurately measured amounts of fluid into a medium, notably the inlet of an analytical instrument. In particular, it relates to needle syringes, especially automated needle syringes.

BACKGROUND OF THE INVENTION

Fluid injection devices, notably needle syringes, and particularly automated devices of these types have gained wide acceptance over the past few decades by industry, and by the medical and scientific communities generally, for use in dispensing small accurately measured quantities of fluid specimens into analytical instruments. A large measure of this success is due to the automation feature, and modern data gathering techniques, which greatly reduce operating manpower without decrease in accuracy. There remains a considerable demand for improved automated devices of these types.

Typically, an automatic fluid injector is constituted of three major sub-assemblies, viz., (a) a syringe, inclusive of a barrel and needle dispensing element which is employed to measure out and convey a fluid specimen directly to the inlet of an analytical instrument, (2) an injector feed assembly for transfer of a fluid specimen from a supply source to the barrel of the syringe, and (3) a magazine into which fluid specimen filled vials are loaded for pick up by the injector feed assembly for transfer to the barrel of the syringe. The syringe, in particular includes a barrel into which a fluid specimen can be loaded, a needle mounted on an end of the barrel, and means for the displacement of the fluid specimen from said barrel via the dispensing end of the needle into said inlet. Typically the displacement means is a plunger which traverses the length of the barrel. Or, the displacement means can be a valve which after passage of the fluid specimen into the barrel can be closed, and thereafter the fluid specimen can be displaced from the barrel by transport of an end of the needle into the barrel to express a fluid specimen from the opposite dispensing end of the needle. The injector feed assembly typically is constituted of a probe sub-assembly inclusive of a pair of concentrically mounted hollow needles, an end of which can be projected into a septum sealed fluid-specimen containing vial for the pick up of said fluid specimen for filling the barrel of said syringe. The probe sub-assembly is separately movably mounted adjacent the syringe, and transfer lines are employed to convey fluid specimens to the barrel of the syringe when the vial is pressurized with a gas to transport the fluid specimen via one of the pair of hollow needles. The magazine transports the fluid specimen-containing septum sealed vials in seratim to a position for pick up by the pair of hollow needles of said probe sub-assembly for delivery to the barrel of said syringe via thrust of the probe through the septum of a vial so that the contents of the vial can be pressurized by delivery of gas from a source through a first flow path provided by the pair of needles of said probe sub-assembly to produce flow of fluid specimen from the vial through a second flow path provided by the pair of needles of the probe sub-assembly to the barrel of the syringe. Such instruments are described, e.g., by reference to U.S. Pat. No. 3,754,443; U.S. Pat. No. 3,824,859; U.S. Pat. No. 3,885,438; U.S. Pat. No. 3,940,995; U.S. Pat. No. 4,000,654 and U.S. Pat. No. 4,044,616. Wherein these instruments have served admirably, there exists an incentive to further simplify the construction of these instruments, as well as to further provide novel instruments for general and specifically defined usages.

OBJECTS

It is, accordingly, a primary object of this invention to fulfill these and other needs.

A particular object of the present invention is to provide a novel fluid injector, notably an automated needle syringe useful for continuously serially withdrawing small quantities of fluid specimens from prefilled septum covered vials, or containers, and injecting accurately measured quantities of the specimens into the inlet of an analytical instrument.

A further and more specific object is to provide a fully automated apparatus of the type generally described of relatively simple construction which can be readily serviced and operated, and which is particularly useful for delivering fluid specimens to an auxillary analytical device, notably a purge and trap concentrator wherein volatile organics are purged from a fluid specimen with an inert gas, sorbed onto a trap, and thermally desorbed from the trap for subsequent chromatographic separation.

THE INVENTION

These and other objects are achieved in accordance with the present invention which embodies improvements in fluid injector devices, notably automatic fluid injector devices which include the usual combination of (A) a syringe which contains a barrel into which a fluid specimen can be loaded, and means for the displacement of the fluid specimen from said barrel via a dispensing end thereof into a medium, (B) a means for the pick up of said fluid specimen for filling the barrel of said syringe, and (C) a magazine for transporting one or more fluid specimen-containing septum sealed vials for pick up by said means (B), supra, for delivery to the barrel of said syringe for subsequent injection into said medium, e.g., the inlet of an analytical instrument. The apparatus combination of this invention embodies improvements in the syringe (A) and in means (B) by virtue of which the more conventional probe assembly is simplified, and in this instance integrated in large part within the syringe assembly.

In brief compass, a preferred syringe assembly and its means for pick up of a fluid specimen from a vial carried by the magazine includes a barrel, a plunger or plunger rod reciprocably mounted in one end of the barrel, a pair of concentric hollow needles of different diameters, the outer larger diameter needle containing a side wall opening communicating with the axial opening therethrough, mounted in the opposite end of the barrel to form an annulus between the external wall surface of said inside smaller diameter needle and the inside wall surface of said larger diameter needle, and a tubular block valve the tubular opening through which the said concentric pair of needles can be projected into a vial carried by the magazine. The block valve is further provided with a pair of lateral channels communicated with said tubular opening thereof such that when the dispensing end of the smaller diameter needle is projected into a vial and immersed in a fluid specimen, gas can be injected via a first lateral opening of said block valve and needle annulus to pressurize the fluid contents of the vial to drive fluid specimen via the axial opening of the small diameter needle into the barrel, on retraction of the plunger rod. On closure of said first lateral block valve opening with the second lateral opening of said block valve opened, the fluid specimen can be displaced from the syringe barrel and expressed via said second lateral block valve opening to an analytical instrument, e.g., a purge and trap concentrator wherein volatile organics are purged from a fluid specimen with an inert gas, sorbed onto a trap, and then thermally desorbed for subsequent chromatographic separation. (Purge and trap concentrators of this type, i.e., Model LSC-2 and Model ALS, are manufactured by the Tekmar Company of Cincinnati, Ohio.)

The syringe assembly of this invention, at the forward end of the barrel, in another of its aspects, is preferably provided with a forward tubular packing, the axial opening through which is communicated with a lateral opening for the transfer to waste of foam, or bubbles, or both, from an initial portion of a liquid specimen obtained from a vial.

In yet another of its aspects, the plunger per se and body portion of the syringe assembly are actuated and moved independently one with respect to the other preferably via motor driven elevator type mechanisms, the upper and lower limits of travel of which are set by limit stop means, preferably microswitches. For actuation of the plunger, the handle portion of the plunger is affixed to a plunger drive, or plate, which is vertically elevated and lowered upon a rotatable threaded shaft driven by a motor. The body portion of the syringe per se is elevated and lowered via attachment of the syringe body to a yoke, or plate, which in turn is attached to a rotatable threaded shaft driven by a motor. The upper and lower limits of the path of travel of the body of the plunger, and plunger, respectively, are set by limit stop means, notably microswitches which are actuated on contact.

The characteristics of a preferred automatic fluid injector, particularly one useful with a purge and trap autosampler, and its principle of operation, will be more fully understood by reference to the following detailed description, and to the attached drawing to which reference is made in the description. The instrument as a whole, and components of the instrument are referred to in terms of reference numerals in the different views that are presented, similar numerals being used in the different figures to designate similar components. In describing certain components, and features thereof, subscripts are used with similar whole numbers to describe duplicate components. Where duplicate components are so referenced in the text, and thereafter a single whole number is used without subscripts to refer to said duplicate components the designation is inteded in the generic sense. In the drawing:

FIG. 1 depicts a top plan view of the instrument, this view showing in particular the relationship and positioning of the sample syringe relative to the carrousel type feed tray which delivers septum sealed specimen-containing vials for sequential loading of a fluid specimen into the syringe.

FIG. 2 depicts a bottom plan view of the instrument, a cover plate having been removed therefrom to show portions of the electrical and automation components, inclusive of electrical wiring, pressure gauges, manifolds, valves, motor mount features, flush and waste bottles, and hose routings.

FIG. 3 depicts a left side elevation view of the instrument, showing particularly the sample syringe, and an adjacent internal standards syringe.

FIG. 4 depicts a second left side elevation view of the instrument with the plate behind the sample syringe and internal standards syringe removed to expose the mechanisms which actuate said pair of syringes.

FIG. 5 depicts a right side elevation view to show in better detail the syringe actuation mechanisms, drive motors which actuate the mechanisms, and electrically actuated limit switches.

FIG. 6 depicts a front elevation view of the instrument.

FIG. 7 depicts a fragmentary side elevation view of the internal standards syringe, and its actuating mechanism.

FIG. 8 depicts a further front elevation view of the instrument, in this instance sections of the walls being cut away to expose internal components of the instrument.

FIGS. 9 (9A) through 16 (16B) depict a series of views of the instrument at different time sequences, as required for describing a complete cycle of operation of the instrument. FIGS. 13 (13A) through 16 (16B) are specifically directed to a purge and clean up operation.

FIGS. 9A and 9B, specifically, are views showing the sample syringe portion of the instrument in detail just prior to the time a fluid specimen is loaded into the syringe via transfer of a liquid specimen from a vial to the barrel of the sample syringe. In these views the first portion of the specimen from the vial which often is a foam or liquid filled with bubbles is discharged to waste. FIG. 9B is an enlarged fragmentary view of the vial valve block, and lower portion of the sample syringe depicted in FIG. 9A.

Figures 10A, 10B:
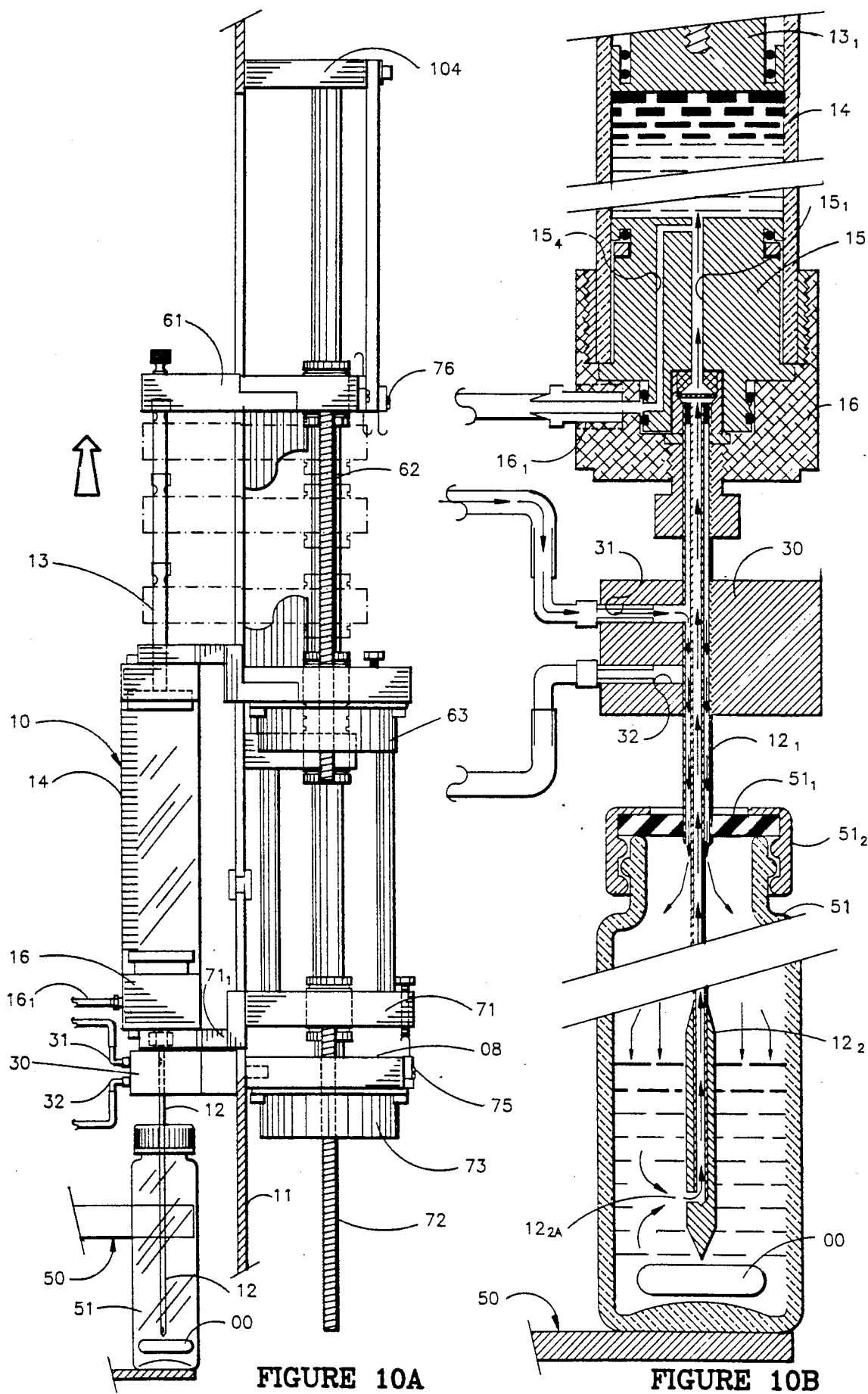
Figures 10C, 11:
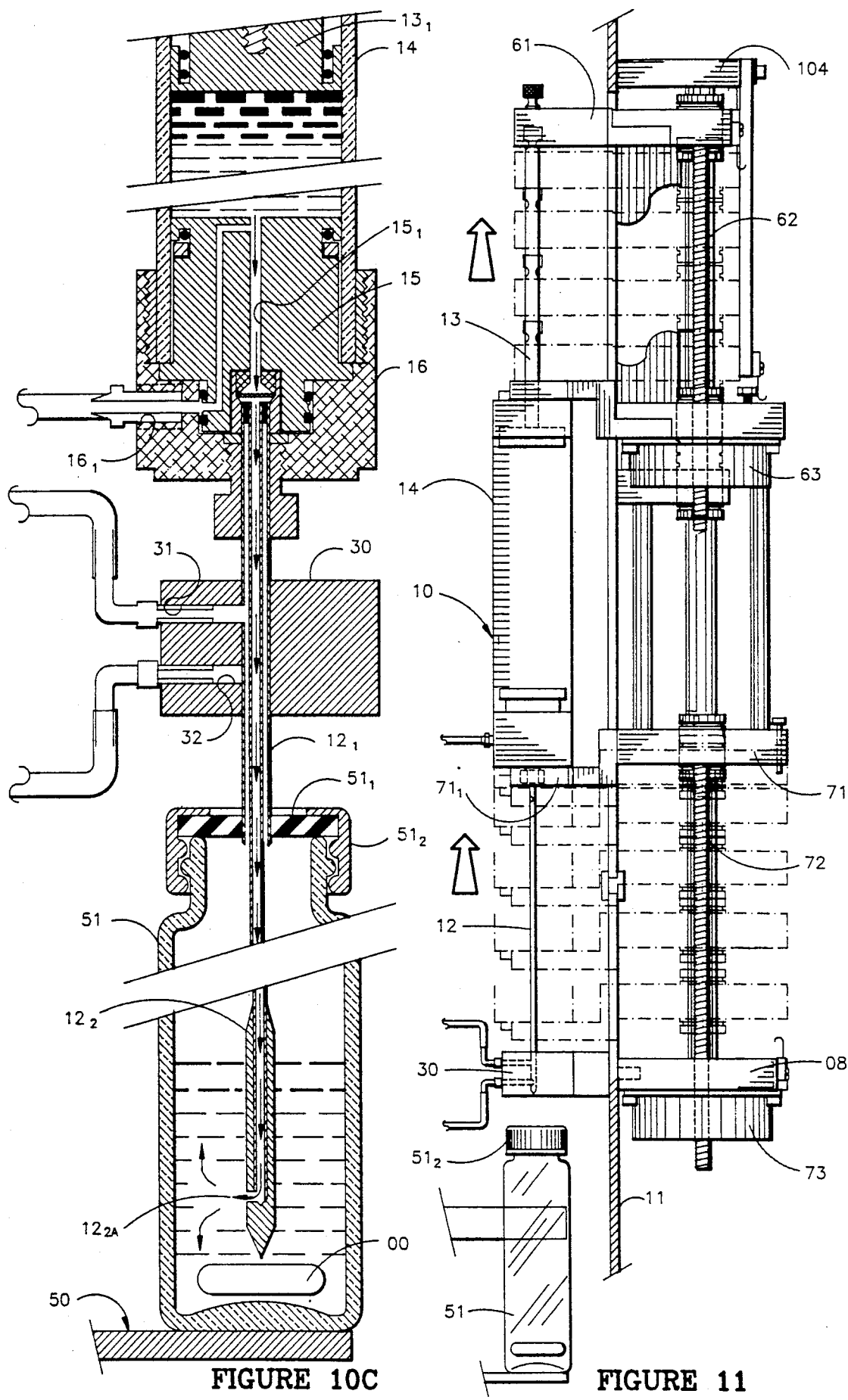

FIGS. 10A and 10B are views show the filling of the sample syringe via transfer of the fluid specimen from a vial into the barrel of the sample syringe; FIG. 10B being an enlarged fragmentary view of the lower portion of the sample syringe, valve block and vial depicted in FIG. 10A. FIG. 10C, taken with FIGS. 9B and 10B, depicts the details of a flush operation the purpose of which is to keep the filter clean.

FIG. 11 depicts a side elevation view of the sample syringe in fully open position, filled with a liquid specimen and now ready for discharge.

Figures 12A, 12B:
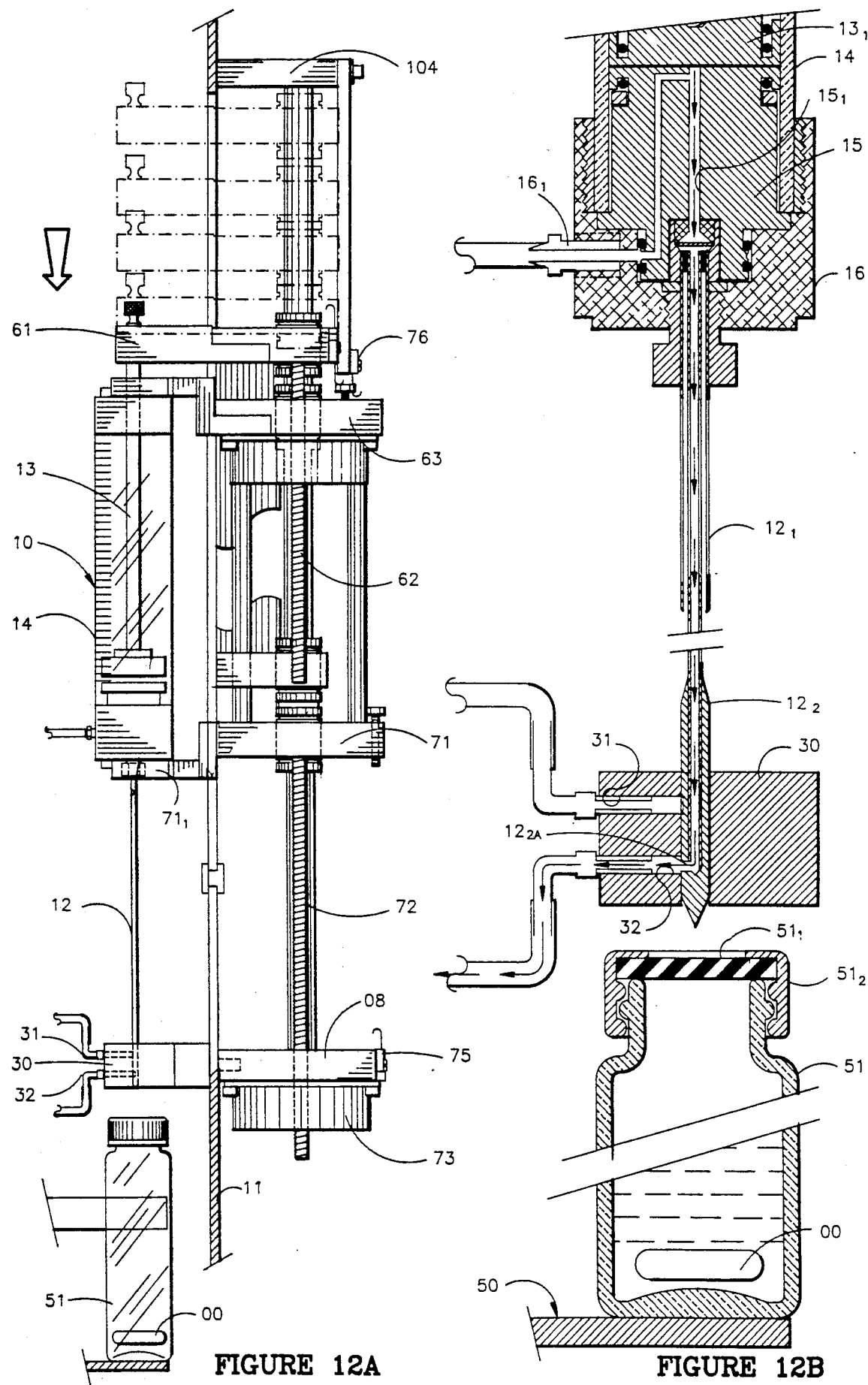

FIGS. 12A and 12B are side elevation views depicting discharge of the liquid specimen from the barrel of the sample syringe to the inlet of an analytical instrument; FIG. 12B is an enlarged fragmentary view of the lower portion of the syringe depicted by reference to FIG. 12A, inclusive of the valve block within which the dispensing end, or needle portion of the sample syringe is located for discharge of the liquid specimen from the barrel of the sample syringe.

FIGS. 13A and 13B are fractional side elevation views depicting the removal of waste or spent sample from the inlet of an analytical instrument such as a purge and trap device, the step specifically depicted by these figures embodying the positioning of the syringe, and its operation, for recycle of excess of the liquid specimen to the barrel of the syringe.

Figures 14A, 14B:
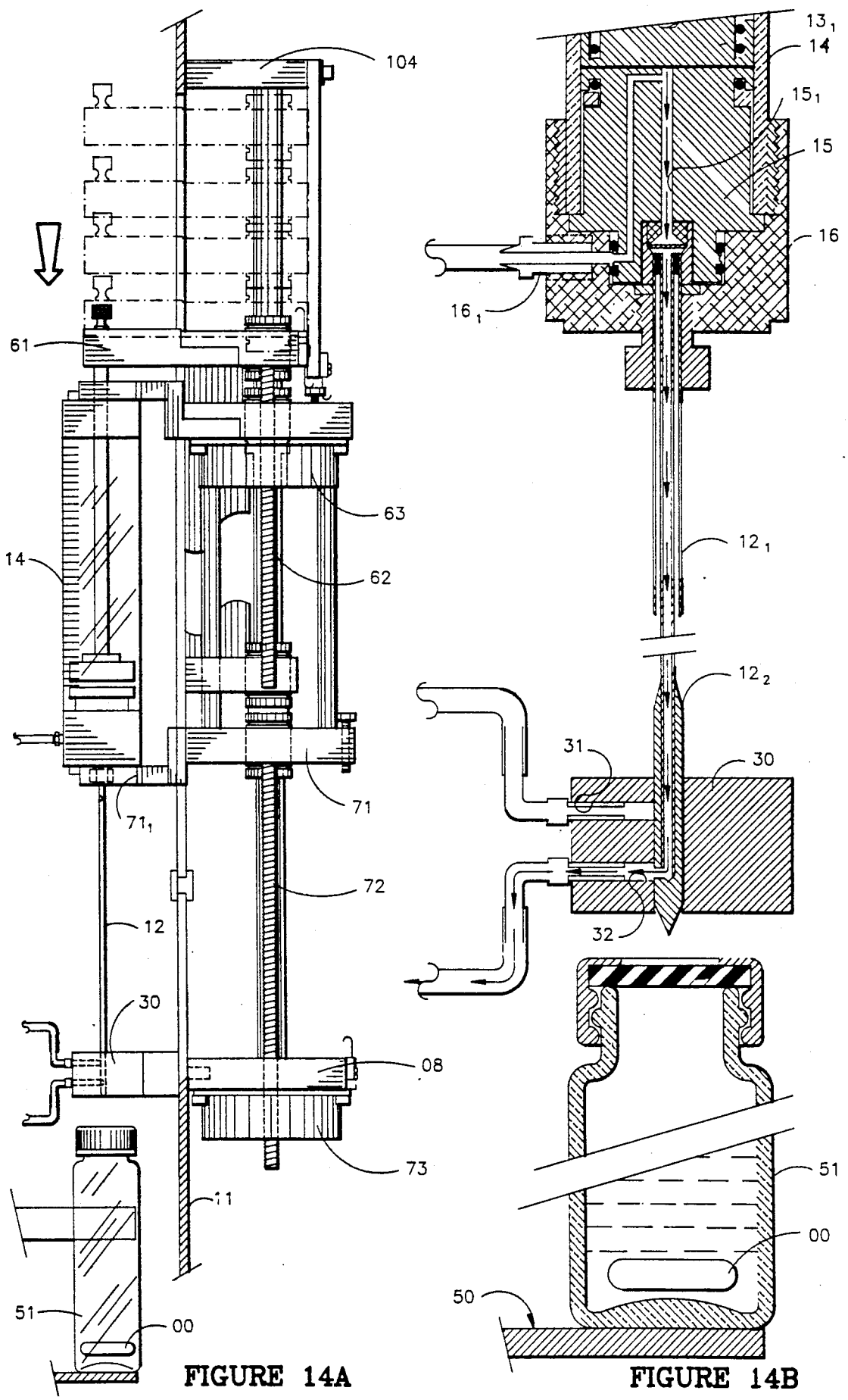

FIGS. 14A and 14B are fractional side elevation views depicting discharge of the recycled excess of the liquid specimen to waste.

Figure 15A:
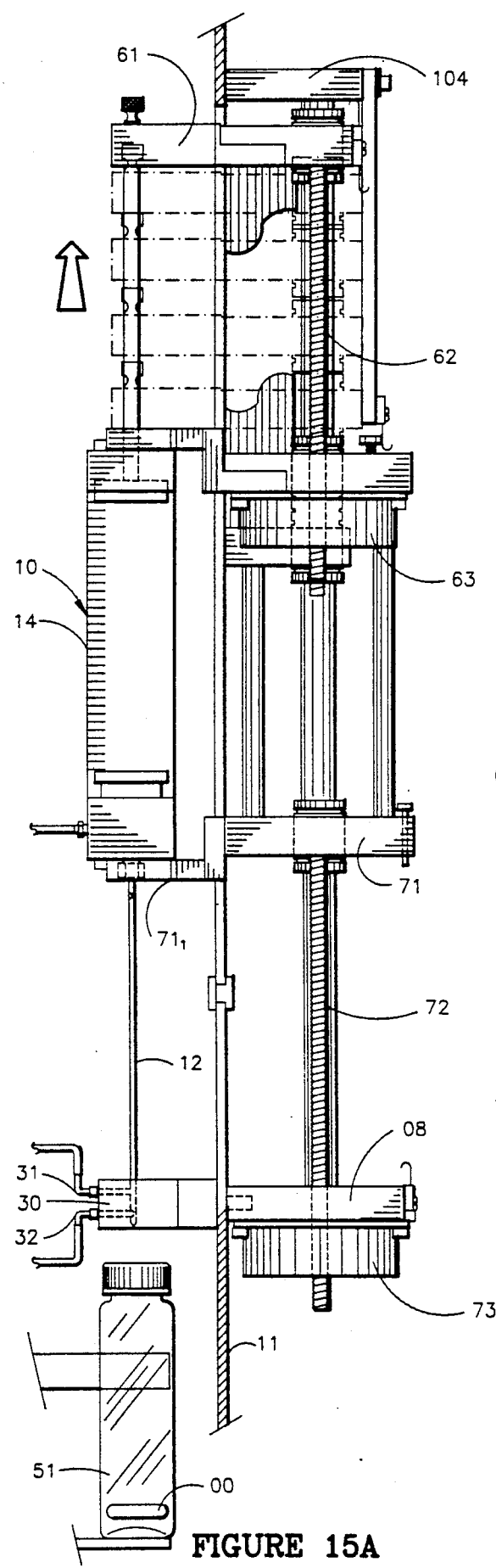
Figure 15B:
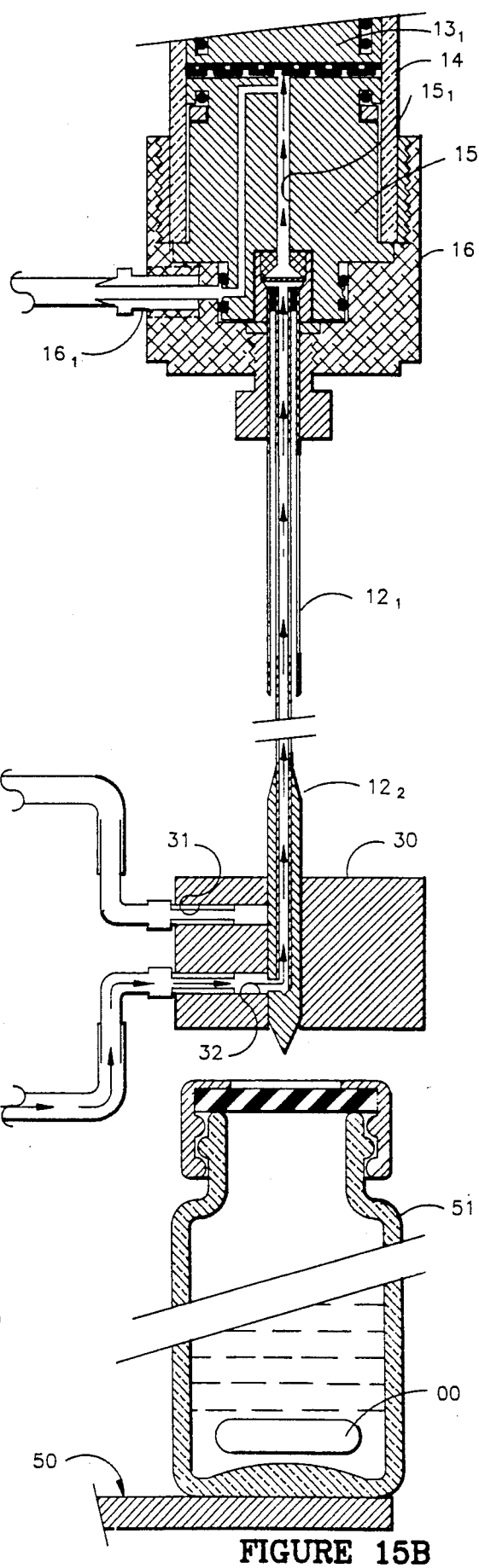

FIGS. 15A and 15B are fractional side elevation views depicting the use of a cleaning fluid, or solvent, for removal of residue from a previous specimen.

FIGS. 16A and 16B are fractional side elevation views depicting discharge of the cleaning solvent to waste.

Reference is made to the figures, first primarily to FIGS. 3, 4, 6 and 8. The principle components of the instrument include generally a sample syringe 10 vertically mounted upon an outer support wall 11, with its dispensing end comprised of a pair of concentric hollow needles 12, viz., $12_1$, $12_2$ (FIG. 9B) projected vertically downwardly through an axial opening, or channel within a valve block 30 the prime functions of which are to purge a liquid specimen of foam, or bubbles, or both, load the liquid specimen into the barrel of the syringe, and provide a means for dispensing the fluid specimen to the inlet of an analytical instrument. Septum covered liquid specimen filled vials 51 are delivered in seratim via a rotatable carrousel feed tray 50 to a position below the valve block 30 for pick up of a fluid specimen from a vial 51 by action of the concentric hollow needles $12_1$, $12_2$ of the sample syringe 10. The upper terminal end of the plunger rod 13 is affixed to an end of a sample syringe plunger drive 61, which is integral and movable with a plate $61_1$ carried upon threaded linear motor shaft 62 reciprocably driven by a first, or no. 1 motor 63. The plunger rod 13 is thus reciprocably vertically movable within the barrel 14 of the syringe 10, while the syringe 10 is held in relatively fixed position, via actuation of the first, or no. 1 motor 63, the limit of movement being defined by an upper no. 3 microswitch 64, and a lower no. 4 microswitch 65, both of which are mounted (with oppositely faced contact ends) upon plate $61_1$ (FIG. 5). The body of the syringe 10 is secured at its lower end to a bottom syringe mount plate 71. The bottom syringe mount plate 71 is mounted, movable upon and carried by threaded linear motor shaft 72 driven by a second motor 73. The pair of concentric needles $12_1$, $12_2$, of the syringe 10 can thus be thrust downwardly through the vertically aligned opening through valve block 30 to project the needles $12_1$, $12_2$ into a vial 51, and subsequently raised into the valve block 30 to purge the initial liquid of foam, or bubbles, and the liquid speciment then injected. The instrument further includes an auxillary, or standard syringe 90 inclusive of a barrel 91, a plunger rod 92 reciprocably mounted within the upper end thereof, and a cannula, or needle 93 affixed within the lower end of the barrel. The upper, or handle end of the plunger rod 92 is affixed to a side of a plunger drive 101 which in turn is integrally mounted upon a plate carried by the threaded linear motor shaft 102 which is reciprocably driven by a third motor 103. The instrument further includes various auxillary components located within the walls and floor of a housing inclusive generally of a blank/wash water gauge 110, waste water bottle 111, blank/wash water regulator 112, wash bottle 113, rotary valve 114, vial pressure regulator 115, vial pressure gauge 116, drive motor 58 for the carrousel feed tray 50, and a keyboard display 117. These several components and sub-assemblies are responsive to automatic control means not per se a feature of this invention. The principle features and overall function of these components and sub-assemblies are described in more detail below.

The sample syringe 10 is an assembly the principle components of which include a barrel 14, constituted generally of a transparent material the outer surface of which is scribed with indicia marks indicative of volume, within the upper end of which is provided a plunger rod 13 and upon the lower end of which is located a pair of concentrically mounted hollow needles 12, a large diameter outer needle $12_1$ and a smaller diameter longer needle $12_2$; the difference between the outside diameter of the upper portion of needle $12_2$ and the inside diameter of needle $12_1$ being sufficient to provide an annulus through which a gas can be passed via pressure gas inlet 31 of valve block 30 to pressurize the liquid contents of a vial 51, as shown e.g., by reference to FIG. 9B. (The lower terminal end of needle $12_2$ it will be noted is of enlarged diameter, an outer concentric tubular segment being welded to the end of the needle to form one piece.) The liquid in vial 51, under pressure, ascends through the axial opening of needle $12_2$. Thus, the lower portion of the concentric pair of needles $12_1$, $12_2$ is shown to have pierced the septum $51_1$ of a vial 51, held in place via an open centered cap $51_2$ atop the vial 51. Continuing for convenience the reference to this figure, the inner lowermost end of the barrel 14 is fitted with a tubular packing 15 the external face of which is provided with an upper o-ring fitting for sealing the packing within the barrel 14. The lower end of the tubular packing 15 is provided with a pair of o-ring fittings for sealing the packing in the threaded end cap 16, threadably engaged to the forward end of the barrel 14. The pair of o-ring fittings for sealing the lower end of tubular packing 15 to the threaded end cap 16 also provides a radial communication channel around the lower end of tubular packing 15 this facilitating the lineup of channels $15_4$, $16_1$ and allowing lateral opening $15_4$ to communicate with nozzle outlet $16_1$ in end cap 16. The centrally located axial opening $15_1$ communicates through the enlarged channel opening of the tubular member $15_2$ with the opening through needle $12_2$. The tubular member $15_2$ contains a filter $15_3$ within an enlarged segment of the axial opening, the upper terminal end of needle $12_1$ is affixed and sealed within the opening through tubular member $15_2$ and the end of needle $12_2$ is sealed at its upper end within the larger diameter opening of needle $12_1$. The tubular packing 15, it will be observed, is further provided with what is in effect a lateral opening $15_4$, one end of which communicates with the upper side of the axial opening $15_1$, and the other with a nozzle outlet $16_1$ in end cap 16. The channel $15_4$ is controlled via a solenoid actuated valve (not shown) to open and close in a controlled sequence. In FIG. 9B, with the plunger head $13_1$ all the way down within the barrel as shown to block, or close the end of channel $15_1$, a solenoid valve (not shown) is opened, and foam and bubbles ascending within the opening $15_1$ are expressed via line $15_4$ to waste. On closure of the solenoid valve to interrupt the flow, and on upward slow withdrawal of the piston head $13_1$ (FIG. 10B) a positive flow of liquid through axial opening $15_1$ fills the barrel without the formation of bubbles, or foam. A positive flow of liquid thus results from the pressure with a vial 51 which actually pushes the liquid into the barrel 14 as the plunger head $13_1$ is retracted; this avoiding the creation of a vacuum which would cause bubble formation in barrel 14 as it is filled.

Figure 3:
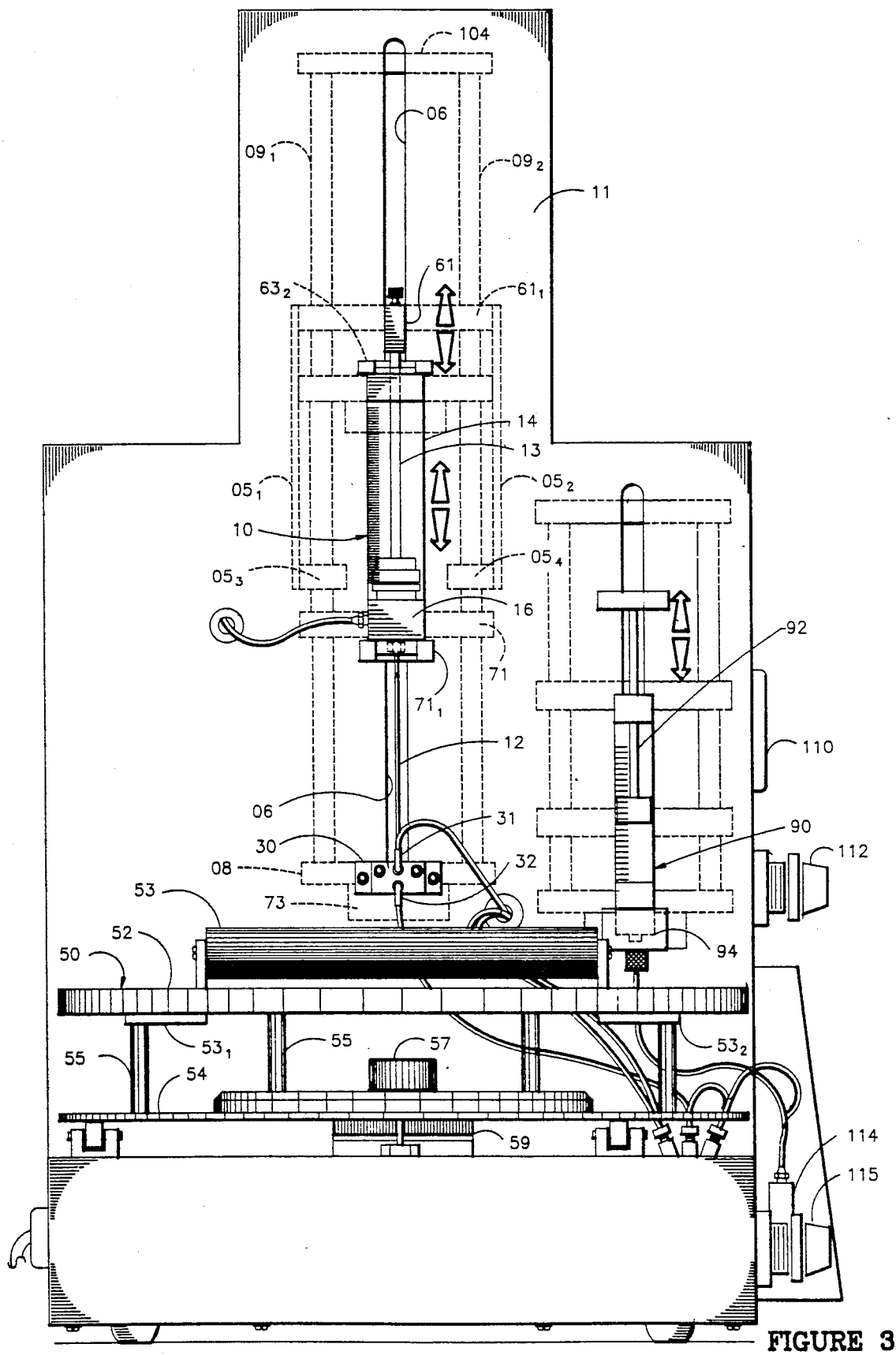
Figure 4:
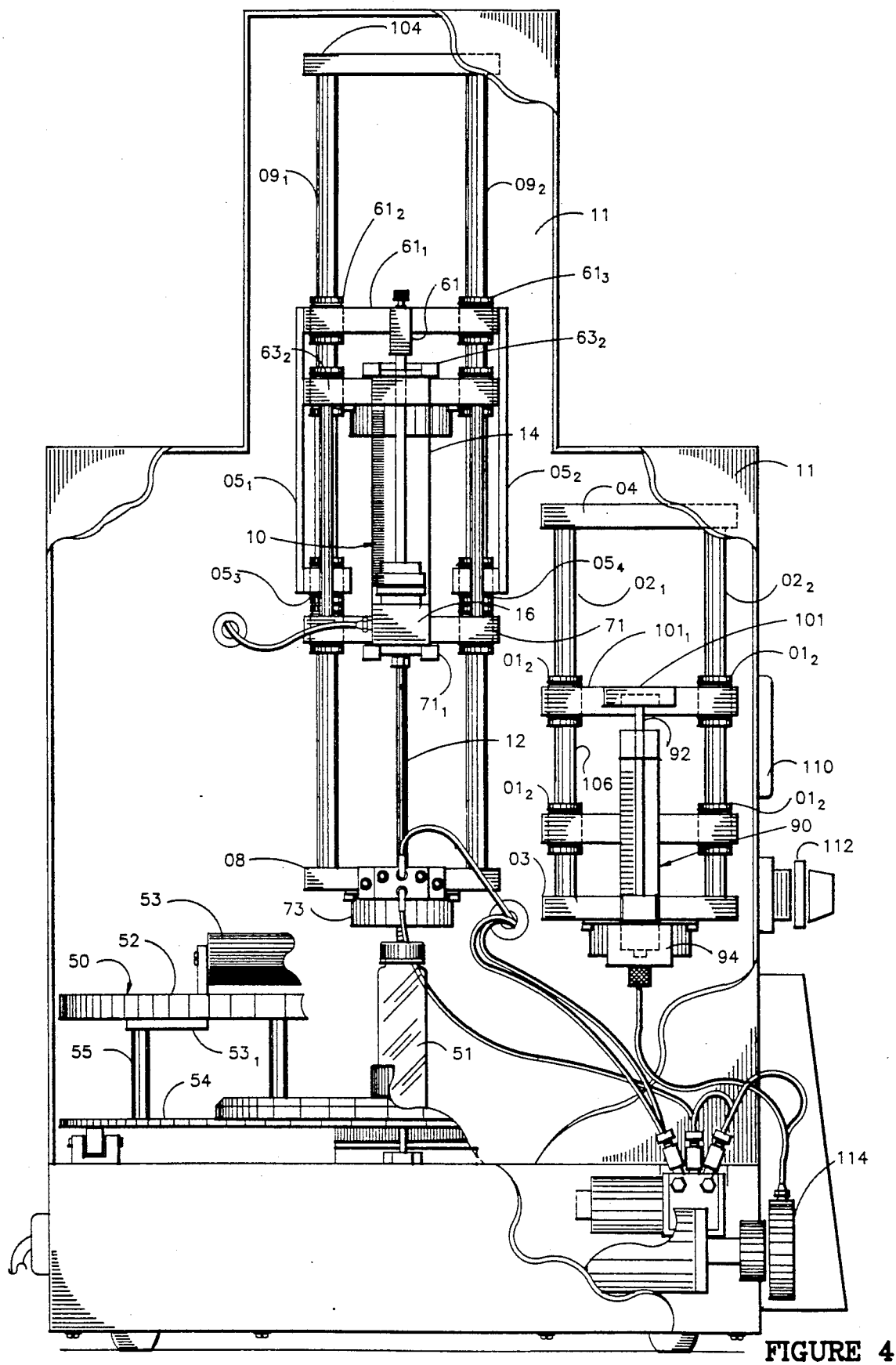
Figure 5:
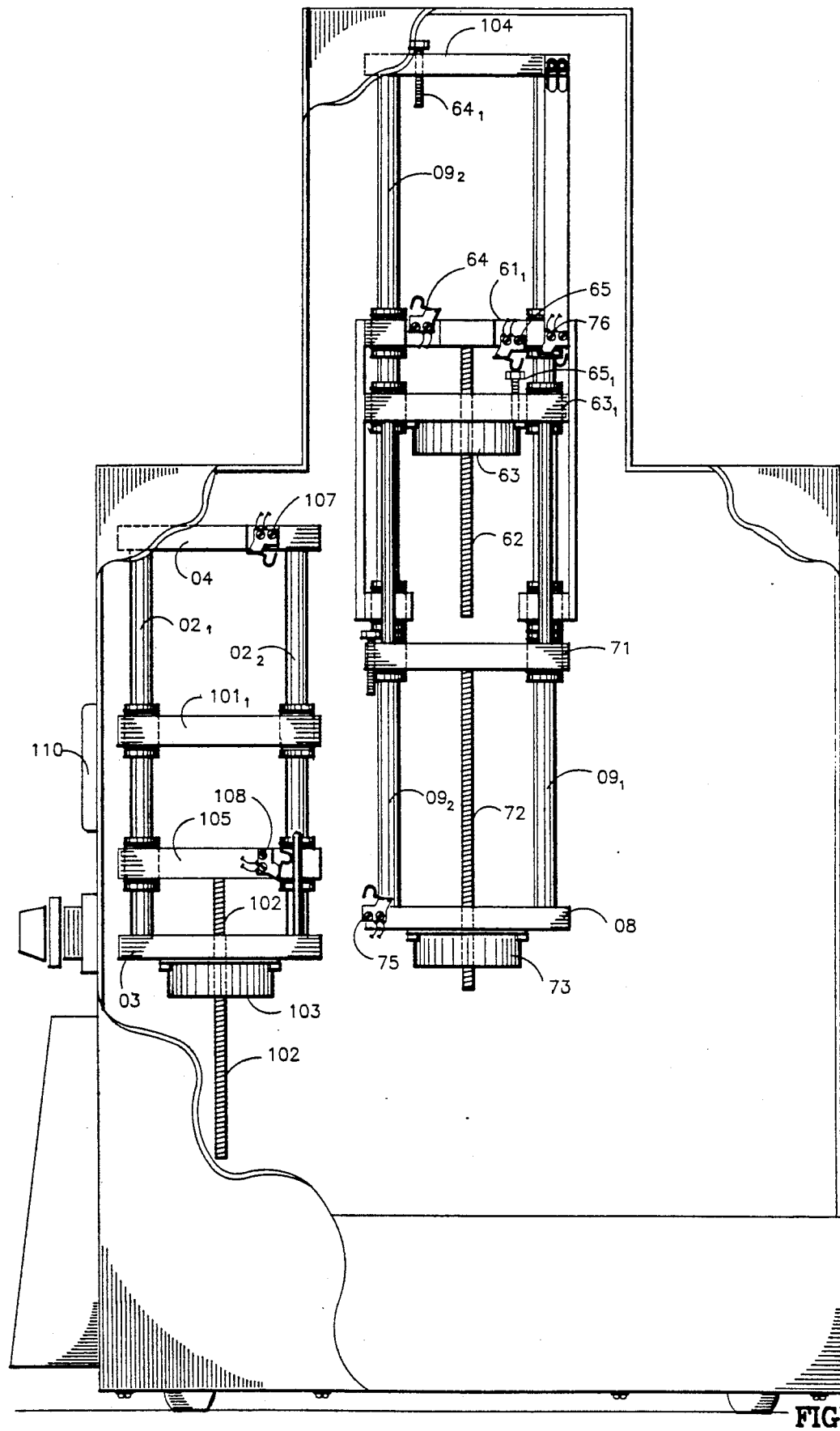
Figure 6:
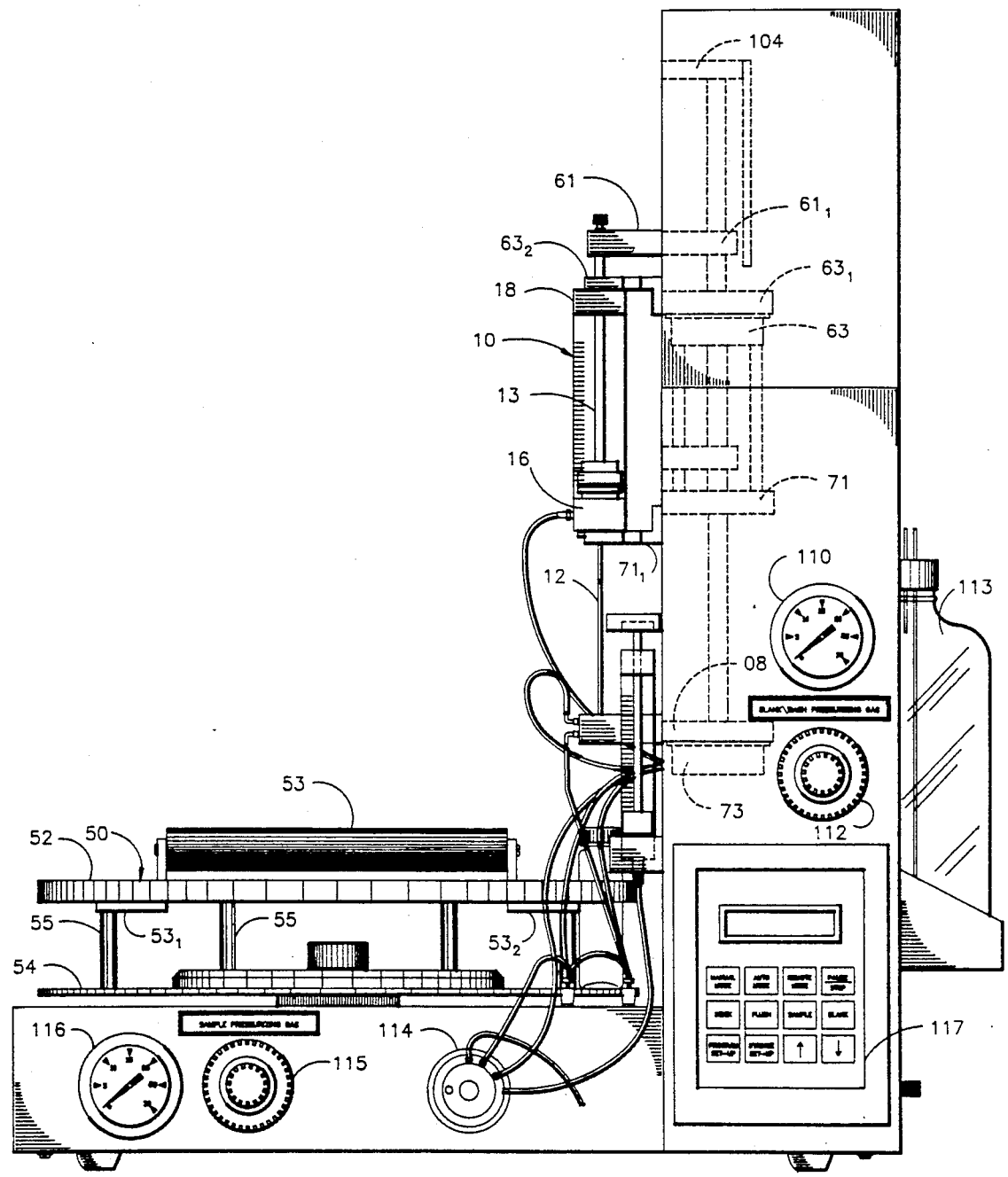

The mechanism which reciprocates the plunger arm 13 within barrel 14 of the sample syringe 10, and the body of the sample syringe 10 per se is best described by specific reference to FIGS. 3, 4, and 5. With reference thereto, it will be observed that the sample syringe 10 is vertically mounted and vertically reciprocably movable upon the wall 11. A frame generally of parallelogram shape is located on the side of the wall 11 opposite that of the sample syringe 10, the frame including a pair of vertical shafts $09_1$, $09_2$ spaced apart and parallelly oriented one with respect to the other, mounted upon a base 08, capped and held rigidly together by a top support plate 104. The plunger rod 13 of the sample syringe 10 is affixed to plunger drive 61 a portion of which is extended through the elongate vertical slot opening 06, and affixed to a plate $61_1$. The plate $61_1$ is provided with alternately disposed openings therethrough, and tubular bearings or collars $61_2$, $61_3$ through which the shafts $09_1$, $09_2$ are extended. The plate $61_1$, and collars $61_2$, $61_3$ to which the plate $61_1$ is affixed, is slidably movable upon the shafts $09_1$, $09_2$. Additional stability is provided for vertically movable plate $61_1$ by parallelly mounted vertically oriented arms $05_1$, $05_2$ which are affixed at their upper ends to plate $61_1$ and at their lower ends to tubular collars, or bearings $05_3$, $05_4$ which ride upon the shafts $09_1$, $09_2$, respectively. In effect, plate $61_1$ is thus a carriage to which the plunger drive 61 is affixed, and it is mounted upon and supported by carriage slide rods, or vertical shafts $09_1$, $09_2$. It is actuated and motor driven to move upwardly and downwardly upon the slide rods $09_1$, $09_2$ to reciprocate the plunger rod 13, relative to the barrel 14 of the syringe in timed sequence to fill and discharge fluid from the barrel 14 of the syringe 10. The plate 71, which is connected via a lower yoke $71_1$ through slot opening 06 to the body of syringe 10, is similarly mounted upon the shafts or slide rods $09_1$, $09_2$—likewise forming in effect a motor driven carriage which vertically raises and elevates the body of the sample syringe 10. Thus, the mechanism operates much in the fashion of a syringe the body of which is held between the fingers of the hand, the plunger operated by the thumb, and the syringe as a whole moved by change in position of the arm and forearm of an operative. The standard syringe 90 is actuated and driven in a much similar fashion, though the body of the syringe via its lower block mount 94 is fixed on wall 11 with only the plunger 92 movable. The frame associated with the standard syringe 90 is constituted of a pair of vertically parallelly oriented, spaced apart shafts $02_1$, $02_2$ supported upon a base 03, with the two upper ends being capped by a top support plate 04. The plunger 92 is vertically movable, upwardly and downwardly, via actuation of plunger drive 101 affixed to the upper plunger plate $101_1$, the plunger plate 101 being mounted via tubular bearings $01_1$, $01_2$ to the slide rods $02_1$, $02_2$.

Returning to the discussion of the specific means of actuation, and operation of the sample syringe 10, the plunger rod 13 per se is actuated and moved relative to the body of the sample syringe 10 via the motor driven mechanism principally located on the opposite side of wall 11 from the syringe body. The upper terminal end of plunger rod 13, it will be observed, extends beyond the confines of syringe barrel upper end cap 18 of the syringe 10 and is affixed via a screw connection to vertically reciprocably movable sample syringe plunger drive 61. The sample syringe plunger drive 61, on its opposite side, is connected to or integral with a plate $61_1$ carried by the threaded linear motor shaft 62 which is reciprocably driven by the linear motor 63 (FIG. 5). The motor 63 is, in turn, supported upon the bottom face of motor support plate $63_1$ to which it is directly connected. The motor 63 thus rotates the threaded linear motor shaft 62 in either direction, as desired, to drive the sample syringe plunger drive 61 upwardly, or downwardly. As a consequence the plunger rod 13, which is slidably fitted within upper fixed yoke $63_2$, is retracted or advanced into the barrel 14 of sample syringe 10. The extent of movement of the sample syringe plunger drive 61 is controlled via microswitches 64, 65, best illustrated by reference to FIG. 5. The microswitch 64, located on top of the plunger drive 61, limits at a given level the upward upward movement of plunger drive 61 by contact of the microswitch 64 with the adjustable downwardly projected screw end $64_1$ extended through top support plate 104. The microswitch 65 limits the downward level of movement of the sample syringe plunger drive 61 when it contacts the upwardly projected adjustable screw end $65_1$ located on support plate $63_1$. Retraction, or upward movement of the plunger rod 13 relative to the syringe body is required in filling the barrel 14, and downward movement relative to the syringe body is required to displace liquid specimen from the barrel 14 of the syringe 10.

The body portion of the sample syringe 10 is affixed via a lower yoke $71_1$ to a bottom syringe mount plate 71 mounted upon the vertical shafts $09_1$, $09_2$, and the bottom syringe mount plate 71 is in turn carried upon the terminal end of threaded linear motor shaft 72. The body of the sample syringe 10 is thus vertically reciprocably movable with said plate 71 upon vertical shafts $09_1$, $09_2$ via rotation of said threaded linear motor shaft 72 by the motor 73 mounted upon the lower face of bottom base plate 08. Downward movement of the body of sample syringe 10 is required to thrust the dispensing end of needle $12_2$ through the septum of a vial 51 to a position near the bottom of said vial, and retraction or upward movement is required to align the sample ejection port $12_{2A}$ in the tapered lower dispensing end of needle $12_2$ with the outlet port 32 of valve block 30 to deliver a fluid specimen via rotary valve 114 and then to, e.g., a sparge tube for uptake by an analytical instrument. The microswitch 75 defines the lower limit, and the microswitch 76 the upper limit in the path of travel by the bottom syringe mount plate 71. Refer e.g., to FIGS. 5, 10B and 12B, respectively.

The valve block 30, it will be observed e.g., by reference to FIGS. 10B and 12B respectively, is provided with a gas inlet 31 and sample specimen outlet 32. The openings 31 and 32 are thus each fitted with an "L" shaped metal tube one end of which is fitted into an opening, respectively, while the outer ends of each are fitted with hose connections such that a pressurized gas e.g., helium gas, can be conveniently introduced into inlet 31, and sample specimen from a vial 51 expressed via rotary valve 114 to an analytical instrument via outlet 32.

Figure 7:
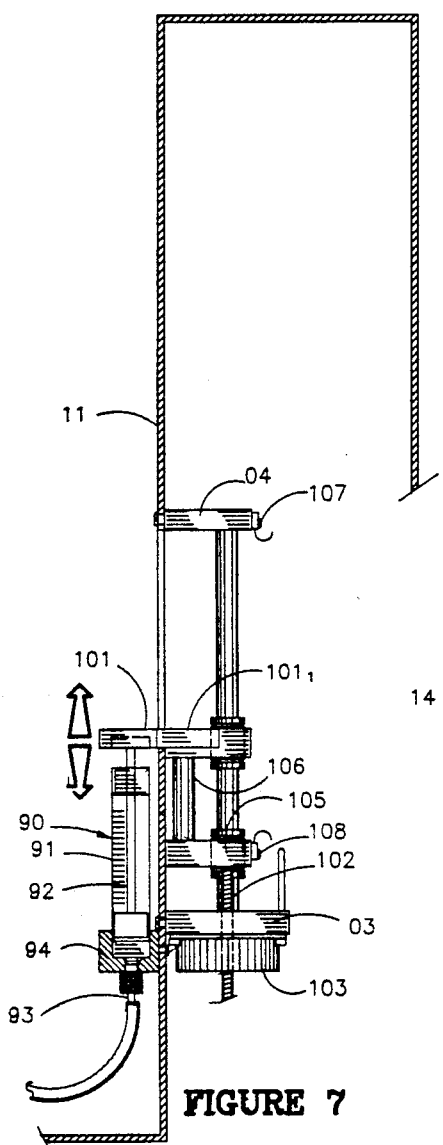

On occasion it is desirable to inject a standard sample into the analytical instrument for comparative purposes, this being accomplished by use of the standard syringe 90. The standard syringe 90 is provided with the instrument for this alternative use, and embodies a barrel 91, generally a barrel of transparent material scribed with indicia marks, cannula or hollow needle 93 provided with a hose connection mounted on the forward end of the barrel 91, and plunger rod 92 mounted in the opposite end of barrel 91. The needle 93 is in communication via said hose connection with rotary valve 114 for the transfer, after the receipt thereof, of a standard specimen to the analytical instrument. Like the sample syringe 10 the standard syringe 90 is mounted on one side of the wall 11, while a plunger actuation mechanism quite similar to the plunger actuation mechanism driving the sample syringe plunger 13 of sample syringe 10, is located on the opposite side of the wall 11. The plunger actuation mechanism for the standard syringe 90 is best described by reference to FIGS. 4, 5 and 7. The mechanism is constituted generally of a pair of spaced apart parallelly aligned vertical shafts $02_1$, $02_2$, at the top of which is located a plate 04 and at the bottom a base plate 03. The shafts $02_1$, $02_2$ constitute in effect tracks upon which a carriage driven by the motor 103, located below the base plate 03, can be vertically reciprocated. The carriage is formed by upper and lower plates $101_1$, 105 separated one from another via tubular spacer elements 106, and affixed via tubular bearings $01_2$ to the shafts $02_1$, $02_2$, respectably, and slidably movable thereupon. The standard syringe 90 is affixed to wall 11 via a lower support 94 and the upper handle portion of plunger rod 92 is removably attachable to standard syringe plunger drive 101, an integral part of plate $101_1$ affixed via tubular spacer elements 106 to lower plate 105 forming a carriage which can be raised and lowered via activation of motor 103 which rotates the threaded liner motor shaft 102 affixed to lower plate 105. Thus, e.g., as shown by reference to FIG. 7, rotation of the threaded linear motor shaft 102 via actuation of motor 103, affixed below the base plate 03, will drive the carriage carrying the upper support plate $101_1$ to which the plunger 92 is attached from an extreme lower point to an extreme upper point below the top support plate $101_1$, carrying with it the plunger 92. A microswitch 107 controls the upper limit of movement, and a microswitch 108 controls the lower limit of movement of the carriage and plunger drive 101 (FIG. 5).

Figure 8:
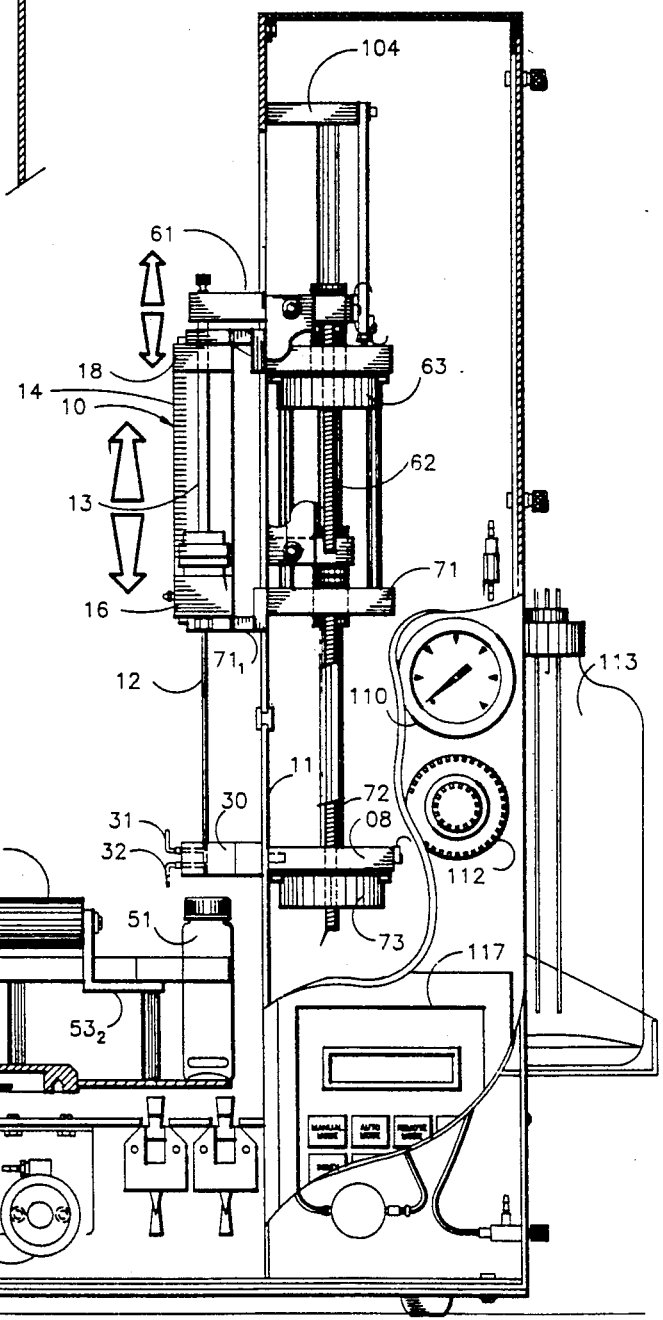

The function of the carrousel feed tray 50, described e.g., by reference to FIG. 8, is to transport septum covered fluid specimen filled vials 51 in seratim to a location below the valve block 30 for pick up by the sample syringe 10. The vials 51 are of an open screw top type enclosed by an elastomeric septum $51_1$ held atop a vial by an open centered cap $51_2$ threadably engaged to the neck of a vial, for pressurization of the liquid specimen contents with a gas, e.g., helium. The contents of a vial 51 are removed by action of the needles $12_1$, $12_2$ as previously described. Suitably, the carrousel feed tray 50 includes a tray comprised of an upper sample tray holder 52 to which is attached a tray handle 53 mounted via brackets $53_1$, $53_2$ to the tray holder, and a sample tray base 54 separated by stand offs 55 providing a unitary tray assembly. On the top of the tray holder 52 is provided a sample tray number ring overlay 56. The composite feed tray mounted upon a sample tray spindle 57 at the geometric center of the instrument floor, and rotated via a motor 58 linked with the tray via a ring gear assembly 59. The tray introduces the vials 51 in consecutive order to a position below the valve block 30 for pick up of a fluid specimen therefrom via action of the sample syringe 10.

Figure 1:
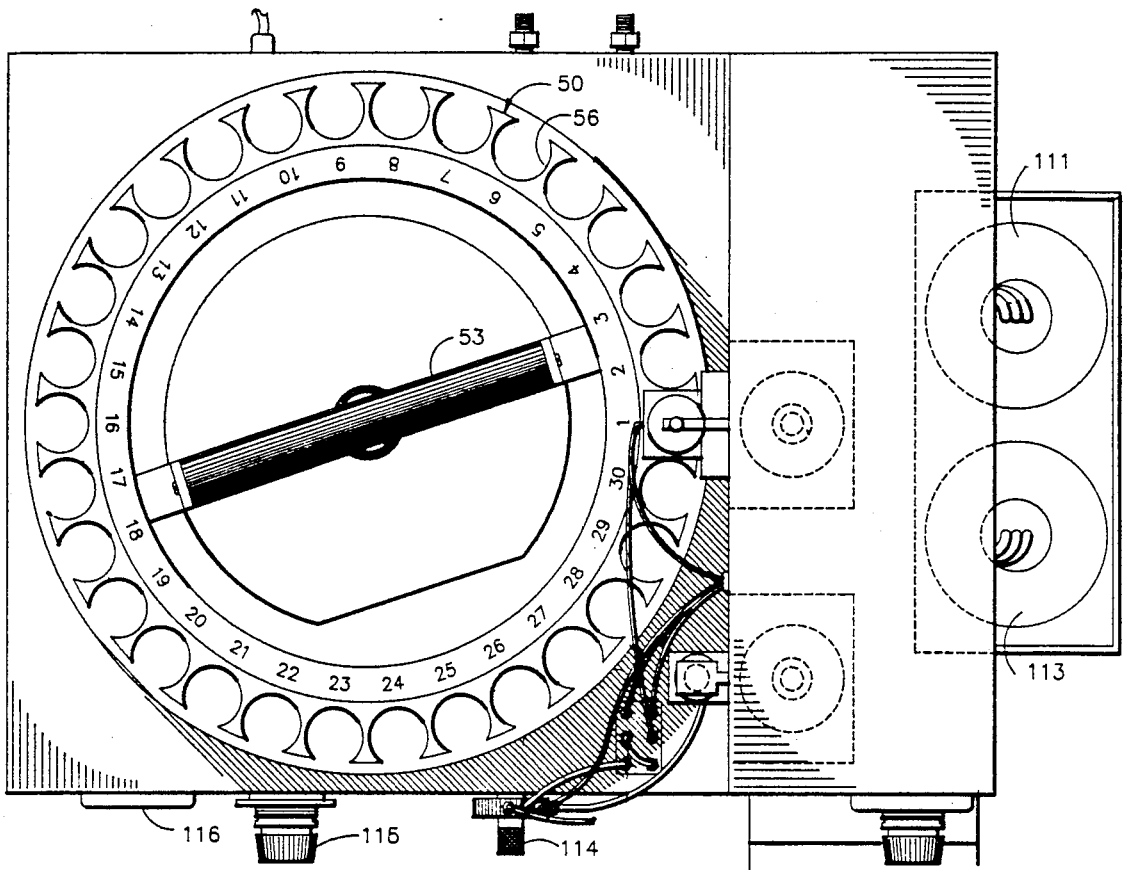
FIGS. 1 through 8 illustrate the instrument at a given point in time, looking at the instrument from a number of locations, to wit.
Figure 2:
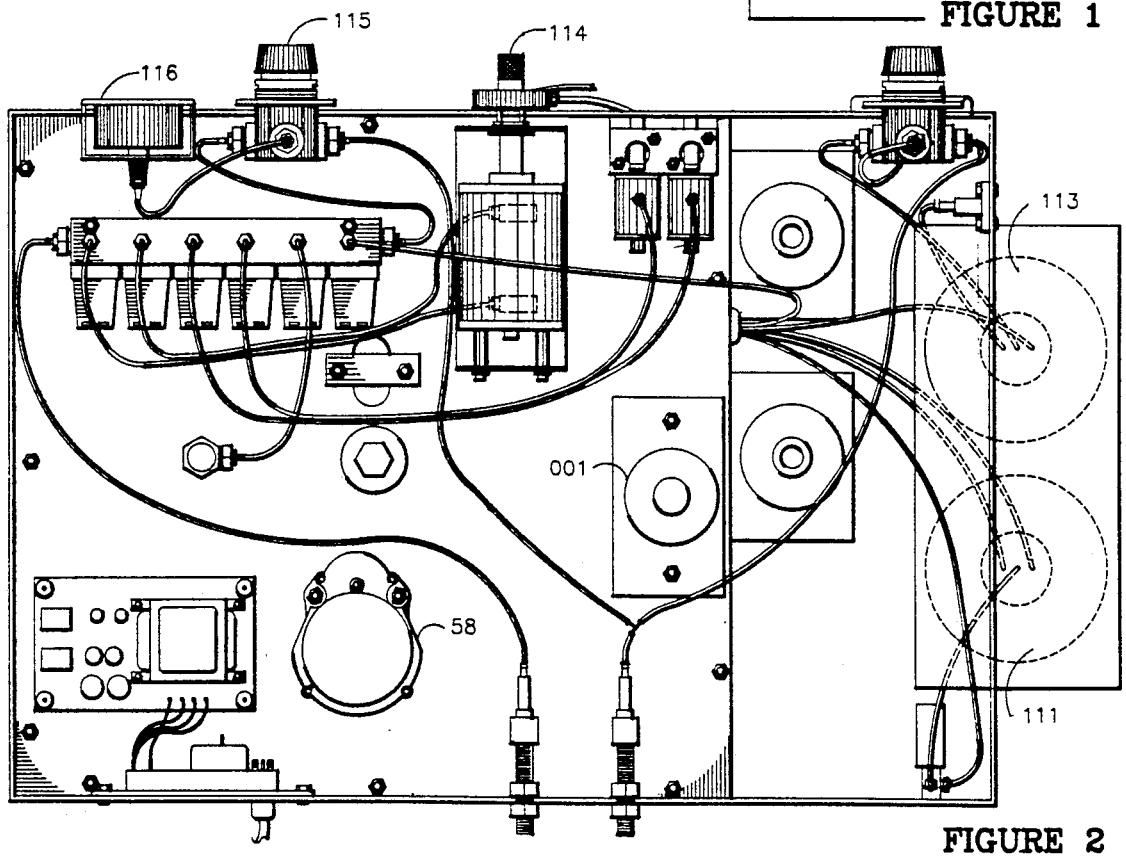

In many sampling operations it is desirable to stir the contents of a vial 51 during withdrawal of a liquid specimen. For this purpose a magnetic stirrer is used, this including the use in a vial 51 of a magnetic material constituting a stir rod unreactive with the fluid specimen. The stir rod 00 is rotated within a vial 51 via rotation of a magnet utilizing a stir motor 001 located at a position below the floor of the instrument. Reference is made to FIG. 2.

The operation of the instrument is best described by reference to FIGS. 9A through 16B. A typical cycle of operation, beginning with the step of loading a fluid specimen from a vial 51 into the barrel 14 of the sample syringe 10 is described by reference to FIGS. 9A and 9B.

In FIGS. 9A and 9B the plunger shaft 13 has been thrust all of way downwardly, the lower terminal end of the needle $12_2$ has penetrated and passed through septum $51_1$ and is located slightly above the bottom of the vial 51, pressurized air is admitted via open solenoid actuated gas inlet 31 and the annulus between needles $12_1$, $12_2$ to pressurize the vial contents, fluid specimen usually containing bubbles and foam is expressed upwardly through needle $12_2$ and opening $15_1$ of the tubular packing 15 to exit therefrom via solenoid valve controlled opening $15_4$ and transferred via solenoid valve to waste bottle 111.

Referring to FIGS. 10A and 10B, the solenoid valve controlling opening $15_4$ is actuated, $16_1$ is now closed, and retraction of the plunger rod 13 to fill the barrel 14 of the sample syringe 10 is near completion. Pressurized liquid specimen from the vial 51 flows upwardly through needle $12_2$ and opening $15_1$ to fill the barrel 14.

Referring to FIG. 10C, in order to backflush the filter $15_3$ of any particulate matter which may have been in the sample from vial 51, the plunger rod 13 is pushed downwardly a short distance to return some of the fluid specimen to the vial 51 via opening $15_1$, and the opening through needle $12_2$, the liquid entering the vial via the side port or opening $12_{2A}$ of needle 12.

Reference is now made to FIG. 11 depicting withdrawal of the sample syringe 10, and retraction of the needle 12 from within the vial 51. The entire sample syringe 10 and plunger rod 13 are lifted upwardly, the positioning of the plunger rod 13 being maintained as the sample syringe 10 is lifted. The side opening $12_{2A}$ of needle 12 on completion of the lift is aligned with the opening 32 of valve block 30 as best depicted by reference to FIG. 12B.

Referring to FIGS. 12A and 12B, the plunger rod 13 is now pushed downwardly via action of the sample syringe plunger drive 61 brought downwardly via rotation of threaded linear motor shaft 62 driven by motor 63. Liquid specimen is displaced from the barrel 14 descending via opening $15_1$, through the filter $15_3$ into the needle 12 to exit via port $12_{2A}$ into the opening 32 of valve block 30 whereupon it is sent to the rotary valve 114 and to the analytical instrument.

FIGS. 13A and 13B, 14A and 14B, 15A and 15B, and 16A and 16B describe the syringe flushing and cleaning operation. Clean wash liquid is withdrawn from the wash bottle 113, after an initial purge, to clean the filter $15_3$ and passageways in preparation for the next cycle of operation. Wash liquid is withdrawn not by the vacuum created in the syringe, but by the pressurized head space in wash bottle 113. The clean wash liquid can also be delivered to the sparge tube of a purge and trap autosampler to flush the tube of any residual contaminants.

In accordance with FIGS. 13A and 13B a slide valve is repositioned, and with lines $16_1$, line 31 closed, the plunger arm 13 is lifted, or withdrawn, via action of the plunger drive 61 on actuation by motor 63, to recycle liquid via line 32, needle opening $12_{2A}$, needle $12_2$ and opening $15_1$ into the barrel 14 of the sample syringe 10.

The recycled liquid, as next shown by reference to FIGS. 14A and 14B, is next sent to waste. Thus, the position of the slide valve is switched. The plunger arm 13 is then pushed downwardly via action of plunger drive 61 actuated by motor 63, and the liquid contents of the barrel 14 are expressed via line 32 to the waste bottle 111.

A cleansing fluid is next pulled into the barrel 14 from wash bottle 113, as shown by reference to FIGS. 15A and 15B. Thus, the positions of the slide valve is again switched, lines $16_1$, 31 remain closed, and the plunger arm 13 is again raised to receive a cleaning liquid via line 32 into the barrel 14 of sample syringe 10.

The opening of needle 12 and barrel 14 thus cleaned, the cleaning liquid is then expressed to waste via line 32 as shown by reference to FIGS. $16_A$ and $16_B$. Thus again, with lines $16_1$, 31 closed, the slide valve is again repositioned and plunger arm 13 is brought down to displace the cleaning liquid from barrel 14 and express the liquid via opening 32 to waste. The instrument is now ready for delivery of a new vial 51 to a position below block valve 30, and initiation of a new cycle of operation.

The instrument is constructed of materials substantially inert or non-reactive to the chemical or corrosive action of the fluid specimens to be measured and dispensed. The barrel of the syringes are normally constructed of glass, but can be constructed of plastic or plastic-like materials. The seals and tubing used in the instrument are normally constructed of rubber or plastic, and the rest of the instrument of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or elastic-like materials, such as natural or synthetic rubbers can also be employed.

The syringes except for the barrels, particularly the needle, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode or particular sequence of withdrawing or delivering fluids, can be made without departing the spirit and scope of the invention, as will be apparent to those skilled in this art.

Having described the invention, what is claimed is:

1. In apparatus useful for the pick up of a fluid specimen from a fluid specimen-containing septum sealed vial carried by a magazine, and injection of preselected quantities of the fluid specimen into an analytical instrument, the combination comprising
    a syringe assembly which includes
    a barrel,
    a plunger rod reciprocably mounted in one end of the barrel,
    a pair of concentric hollow needles of different diameters, an outer larger diameter needle containing a side wall opening communicating with the axial opening therethrough, mounted in the end of the barrel opposite the plunger to form an annulus between the external wall surface of said inside smaller diameter needle and the inside wall surface of said larger diameter needle,
    means for reciprocation of the plunger rod within the barrel of the syringe,
    means for the reciprocal movement of the syringe barrel,
    a tubular block valve the tubular opening through which said concentric pair of needles can be projected into a vial carried by said magazine and positioned in-line therewith, said valve further including a pair of lateral channels communicated with said tubular opening, the first of said lateral channels fluidly communicating with a pressurized gas, the second of said lateral channels adapted to be connected to said analytical instrument,
    whereby, when the dispensing end of the pair of needles is projected through the septum into a vial and an end of the smaller diameter needle immersed in a fluid specimen, gas is passed via the side wall opening of the large diameter needle and the first lateral opening of said block valve via the needle annulus to pressurize the fluid contents of the vial and drive fluid specimen into the axial opening of the small diameter needle, and on retraction of the plunger rod into the syringe barrel, and on the closure of said first lateral block valve opening and opening of the second lateral block valve opening, the fluid specimen can be displaced from the syringe barrel and expressed via said second lateral block valve opening to the analytical instrument.

2. The apparatus of claim 1 wherein the syringe and block valve are mounted on the vertical wall of a housing, and the means for vertical reciprocation of the plunger rod and syringe body are located on the opposite side of the wall on which the syringe and block valve are located, while the block valve is maintained in fixed position on the side of the wall whereon the syringe is mounted.

3. The apparatus of claim 1 wherein means for reciprocation of the plunger rod and syringe barrel are comprised of a vertical frame support,
    a motor driven sample syringe plunger drive located on said vertical frame support operatively connected to said plunger rod for vertical reciprocation of same within the syringe barrel,
    a motor driven syringe mount plate located on said vertical frame support operatively connected to said syringe for vertical reciprocal movement of said syringe,
    and stop means located on said frame support which define the upper and lower limits of vertical movement, respectively, in the operation of the syringe.

4. The apparatus of claim 3 wherein the plunger drive and syringe mount plate are each affixed to a threaded vertical shaft located upon the support frame, and each threaded shaft is rotated independently in either direction by a linear motor mounted upon the frame to move the plunger drive and syringe mount plate, respectively, upwardly and downwardly to project or withdraw the plunger rod within the syringe barrel, and to move the syringe downwardly to pick up fluid specimen from a vial for loading into the syringe barrel, or upwardly to discharge the contents of the syringe barrel.

5. In a fluid apparatus for the injection of preselected quantities of a fluid specimen into an analytical instrument wherein there is included the combination of
    (A) a syringe constituted of
        a barrel into which a fluid specimen can be loaded, and a plunger rod reciprocally mounted in one end of the barrel for opening the barrel for receipt of fluid specimen, and for displacement of fluid specimen from the barrel, (B) an injector feed assembly constituted of a pair of concentrically mounted needles of different diameters, each provided with an axial opening therethrough, an outer larger diameter needle containing a side wall opening communicating with the axial opening therethrough, and an inner needle of sufficiently small diameter to form an annulus between the external surface of said inner needle and the internal surface of said outer tubular needle, and (C) a magazine for transporting one or more fluid specimen-containing septum sealed vials, and serially positioning a vial for the pickup of a fluid specimen therefrom via projection of the dispensing end of said concentric pair of needles of said injector feed assembly (B) through the septum of a vial, gas being passed via the side wall opening of the large diameter needle through the needle annulus to pressurize the fluid contents of the vial to drive fluid specimen from the vial through the axial opening of the small diameter needle for transfer to the barrel of the syringe, the improvement wherein an end of the outer larger diameter needle of the injector feed assembly (B) containing the side wall opening is mounted directly within the end of the barrel opposite that in which the plunger is mounted, the syringe (A) and injector feed assembly (B) thus forming a unitary assembly, and (D) a tubular block valve through the tubular opening of which said concentric pair of needles can be projected into a vial carried by said magazine and positioned in-line therewith, said valve further including a pair of lateral channels, the first of said lateral channels fluidly communicating with a presurized gas, the second of said lateral channels adapted to be connected to said analytical instrument, such that when the concentric pair of needles of said feed injector assembly (B) is projected through the tubular opening, through a vial septum and into a vial carried by the magazine, and an end of the smaller diameter needle immersed in a fluid specimen, gas can be passed via the first lateral channel of said block valve, the side wall opening of the large diameter needle, and via the needle annulus to pressurize the fluid contents of the vial and drive fluid specimen into the axial opening of the small diameter needle, and on retraction of the plunger rod into the syringe barrel, and on closure of said first lateral block valve channel and opening of the second lateral block channel, the fluid specimen can be displaced from the syringe barrel and expressed via said second lateral block valve channel to the analytical instrument.

6. The apparatus of claim 5 wherein the end of the syringe barrel to which the outer larger diameter needle of the injector feed assembly (B) is directly attached contains a tubular packing, a lateral opening in communication with the tubular opening of said packing, and the axial opening of the smaller diameter needle is in communication with the tubular opening through said packing whereby, with the forward end of the plunger rod closing the tubular opening within said packing, an initial portion of the fluid specimen from a vial which often contains foam, or bubbles, can be expressed via said lateral opening of the packing to waste, the lateral opening then closed, and the plunger rod retracted to load fluid specimen into the syringe barrel.

7. The apparatus of claim 5 wherein the syringe and block valve are mounted on the vertical wall of a housing, and drive means are provided to vertically independently reciprocate the plunger rod portion of the syringe, while the block valve is maintained in fixed position upon the wall.

8. The apparatus of claim 7 wherein the drive means is comprised of a vertical frame support, a motor driven sample syringe plunger drive located on said vertical frame support operatively connected to said plunger rod for vertical reciprocation of same within the syringe barrel, a motor driven syringe mount plate located on said vertical frame support operatively connected to the body of said syringe for vertical reciprocal movement of said syringe, and stop means which define the upper and lower limits of vertical movement, respectively, in the operation of the syringe.

9. The apparatus of claim 8 wherein the plunger drive and syringe mount plate are each affixed to a threaded vertical shaft located upon the support frame, and each threaded shaft is rotated independently in either direction by a linear motor mounted upon the frame to move the plunger drive and syringe mount plate, respectively, upwardly and downwardly to project or withdraw the plunger rod within the syringe barrel, and to move the syringe downwardly to pick up fluid specimen from a vial for loading into the syringe barrel, and upwardly to discharge the contents of the syringe barrel.

* * * * *